United States Patent [19]

Jenkins et al.

[11] 4,304,752

[45] Dec. 8, 1981

[54] DETECTION OF TRACER MATERIALS IN THE ATMOSPHERE

[76] Inventors: Anthony Jenkins, c/o Analytical Instruments Limited, London Rd., Pampisford, Cambridge; James E. Lovelock, Coombe Mill, St. Giles on the Heath, Launceston, Cornwall both of England

[21] Appl. No.: 23,140

[22] Filed: Mar. 23, 1979

[51] Int. Cl.³ ...................... G01N 27/00; G01N 31/10

[52] U.S. Cl. .................................... 422/98; 23/232 E; 250/304; 250/382; 422/94; 422/78

[58] Field of Search ............... 23/230.3, 230.6, 232 E; 422/83, 89, 94, 90, 93, 96, 70, 78, 98; 250/304, 382, 379, 383, 389; 423/219, 580

[56] References Cited

U.S. PATENT DOCUMENTS

| | | | |
|---|---|---|---|
| 1,960,212 | 5/1934 | Walker | 423/219 |
| 2,582,885 | 1/1952 | Rosenblatt | 423/580 X |
| 3,420,618 | 1/1969 | Fleming | 423/219 |
| 3,699,342 | 10/1972 | Jenkins et al. | 250/289 X |
| 3,832,137 | 8/1974 | Mlinko et al. | 23/230.3 |
| 3,883,739 | 5/1975 | Jenkins | 422/90 |
| 3,997,297 | 12/1976 | Jenkins et al. | 23/232 E |
| 4,019,863 | 4/1977 | Jenkins et al. | 23/232 E |
| 4,166,379 | 9/1979 | Bradshaw | 250/383 X |

*Primary Examiner*—Michael S. Marcus
*Attorney, Agent, or Firm*—Anthony J. Casella

[57] ABSTRACT

As oxygen is an electron absorber it is desirable, when monitoring an atmospheric flow for the presence of tracer materials capable of detection in an electron capture detector, to remove the oxygen from the flow to the detector. The invention introduces a hydrogen supply directly into the atmospheric flow to allow the hydrogen to combine catalytically with the oxygen content of the flow to form water or water vapor. The thus formed water or water vapor is extracted from the flow proceeding to the detector. The reaction can occur within a palladium or palladium alloy conduit forming a part of the flow path to the detector.

2 Claims, 2 Drawing Figures

31 32 33 34 35 36 37 33' $H_2$ 38' 38 39

DETECTION OF TRACER MATERIALS IN THE ATMOSPHERE

The present invention concerns an apparatus for detecting the presence of tracer materials in the atmosphere.

An electron capture detector is an extremely sensitive instrument and can detect the presence of minute concentrations of electron absorbers in a carrier flow through the detector. The carrier flow should be an inert gas such as nitrogen or argon which cannot elicit a response from the detector. However, in practice, the detector can be required to detect the presence of trace materials in an atmospheric flow and as oxygen is itself an electron absorber which can give rise to spurious and misleading signals it becomes desirable to eliminate or nullify the oxygen content of the atmospheric flow into the detector.

According to the present invention there is provided an apparatus for monitoring the atmosphere for the presence of tracer materials capable of detection in an electron capture detector, the apparatus comprising an electron capture detector, a flow path for conveying an atmospheric flow to the detector, the flow path including a region at which the oxygen content of the atmosphere combines with hydrogen to form water or water vapour, a hydrogen supply means, means for introducing hydrogen from the supply directly into the atmospheric flow at a position upstream of said region and means downstream of said region for removing the thus formed water or water vapour from the flow proceeding to the detector.

Preferably, the region comprises a palladium or palladium alloy conduit containing a catalyst such as palladised asbestos.

The invention will be described further, by way of example, with reference to the accompanying drawings: in which.

Figure 1:
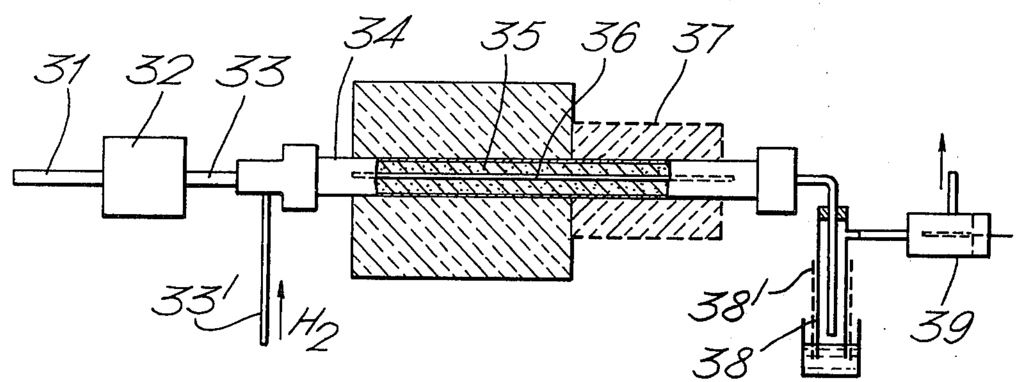
FIG. 1 is a diagrammatic representation of one embodiment.

In FIG. 1, the atmosphere being sampled is drawn into the apparatus through a probe or nozzle 31 by means of a pump 32. From the pump the flow passes along a tube 33 and hydrogen is introduced into the flow by way of a tube 33[1] connected to a suply of hydrogen. The amount of hydrogen introduced into the flow is in excess of that required to combine with the oxygen in the sampled atmosphere.

The mixture of sample and hydrogen enters a palladium or palladium alloy tube which is surrounded by a heat insulating jacket. The tube 34 contains a catalyst 35 such as palladised asbestos for the hydrogen/oxygen reaction. The catalyst is packed loosely in the tube 34 about a rod 36, of heat conducting material, such as a metal rod, preferably a silver rod, which is arranged centrally within the tube 34. The rod 36 serves to distribute the heat of reaction along the length of the tube 34. The rod 36 reduces the temperature gradient over the initial length of the tube 34 so as to avoid a localised high spot and conducts heat to the downstream end of the tube 34 so that this downstream end can be maintained at a temperature in the region of or above 250° C.

The hydrogen reacts with the oxygen content of the sampled atmosphere to form water vapour. Excess hydrogen can diffuse through the wall of the tube 34 over the region 37 to react with the oxygen of the surrounding atmosphere to form water vapour at the outside surface of the tube. The region 37 comprises a heat insulator which maintains the tube 34 at an elevated temperature while at the same time allowing the atmospheric oxygen to pass therethrough from the surrounding atmosphere to the outside surface of the tube where the oxygen reacts with the excess hydrogen passing outwardly through the wall of the tube. Therefore, over the region 37 excess hydrogen is removed from the flow passing along the tube 34 and this flow will be devoid of oxygen. The emerging flow from the tube 34 therefore comprises nitrogen, water vapour and any tracer materials or other constituents present in the sample and which survive the passage through the tube 34. The water vapour is removed in the trap 38 and the flow proceeds to an electron capture detector 39 which detects the presence of any tracer materials. The flow from the trap 38 can include a dryer (not shown) such as a bed of calcium chloride. The trap 38 has a wick 38[1] which dips into the collected water and extends about the flow path. Evaporation at the wick assists in the cooling of the trap.

Conveniently the pump 32 draws the sample into the apparatus at a rate which can be from 50 ccs./minute to 100 ccs./minute. The pump 32 can be connected to the exhaust from the detector 39.

Figure 2:
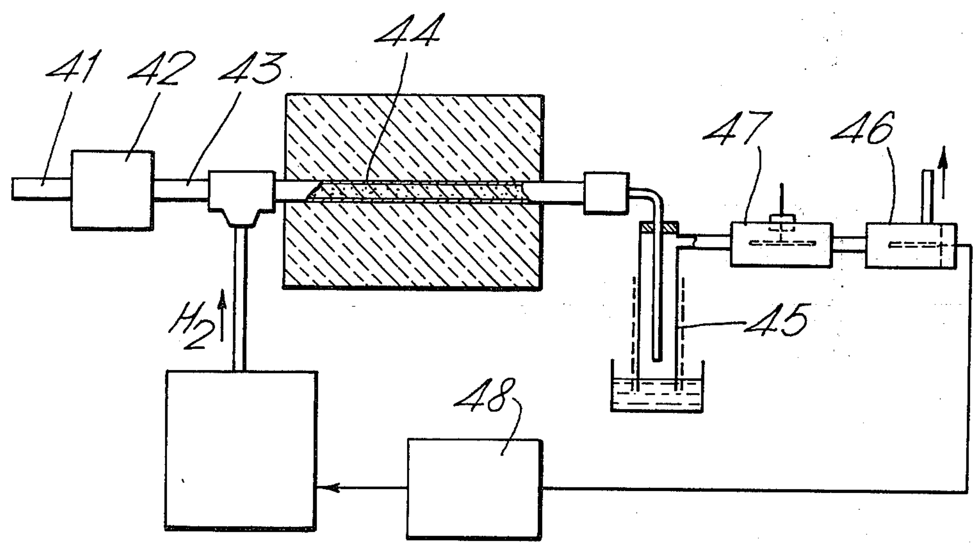
FIG. 2 is a diagrammatic representation of a second embodiment.

In the alternative embodiment of FIG. 2 the atmosphere being sampled is again drawn into the apparatus through a probe or nozzle 41 by means of a pump 42. Hydrogen from a supply is introduced into the flow leaving the pump along tube 43. This portion of the apparatus is therefore identical to that of FIG. 1.

The sample/hydrogen mixture enters a tube 44 which is loosely packed with a catalyst for the hydrogen/oxygen reaction. An example of a suitable catalyst is palladised asbestos. The tube 44 is surrounded by a heat insulating jacket. The flow emerging from the tube 44 passes through a water trap 45 before proceeding to an electron capture detector 46.

The embodiment of FIG. 2 differs from that of FIG. 1 in that the tube 44 is not formed from palladium or a palladium alloy. Consequently hydrogen cannot diffuse through the wall of the tube 44 and as a result it is undesirable to allow an excess of hydrogen to enter the sample flow along the tube 43. In FIG. 2 it is not possible to remove excess hydrogen in the manner of FIG. 1.

In FIG. 2 the amount of hydrogen entering the sample flow is arranged to be just sufficient to react with and remove all oxygen from the flow within the tube 44. If this condition is met the flow leaving the tube 44 comprises the same constituents as in the embodiment of FIG. 1.

To ensure the correct ratio of atmospheric oxygen to hydrogen in the tube 44 it is required to determine either the oxygen concentration or the hydrogen concentration. This can be achieved passing the flow from the water trap 45 through a vapour switching valve 47 before entry into the detector 46. The switching valve 47 can be an ionisation chamber with means for switching the potential thereacross between high and low values. Such an arrangement is disclosed in British Patent Specification No. 1,482,611. If the sample flow contains a strong and a weak electron absorber, the weak electron absorber content of the flow leaving the switching valve 47 remains substantially constant but the strong electron absorber content fluctuates as the potential across the valve 47 is varied between high and low values. The output of the detector 46 therefore comprises a fluctuating component resulting from the strong absorber and a substantially constant component resulting from the weak absorber in the gas flow. In this case the strong absorber will be the tracer material which is to be detected while the weak absorber is oxygen. The constant component output from the detector, which is an indication of the oxygen concentration entering the detector, is used to control a servo system 48 to control either the incoming air or hydrogen supply. The system functions to maintain the constant component at a zero value whereby all the oxygen reacts with the hydrogen in the tube 44 to form water vapour.

The pump 42 can be a variable speed pump and the system can be arranged to control the pump speed such that the amount of air, and hence oxygen, drawn into the apparatus is just sufficient to react with the constant hydrogen supply so that all the hydrogen and oxygen combine to form water vapour within the tube 44.

Alternatively, the hydrogen supply can be controlled by a variable restriction in a fine bore tube in series with a pressure regulator in the hydrogen supply. The restriction can be varied by passing an electric current along the tube to change the temperature.

As a further example, the hydrogen supply can be provided by an electrolytic cell. The control of the hydrogen supply can be obtained by varying the current through the cell.

It is always possible that the sampled atmosphere will contain other constituents which are also electron absorbers capable of producing unwanted signals in the detection. In addition to the removal of oxygen by the hydrogen it is also possible to remove or neutralise other unwanted constituents such as oxides of nitrogen, halocarbons such as carbon tetrachloride, chlorofluorocarbons and tetrachloroethylene in the same manner and at the same time as the oxygen. Further, by controlling the temperature of the reactor it is possible to selectively remove different tracer materials from the flow to the detector. For example, $SF_6$ can pass through the reactor when the temperature is between about 250° to 300° C. but is eliminated at higher temperatures. Perfluorocarbons are unaffected up to temperatures of about 350° to 400° C.

As an alternative to palladised asbestos other catalysts considered suitable for oxygen removal are platinum, nickel and their alloys.

The ivention can find use in monitoring the outfall from chimneys by seeding the effluent with a tracer. Another application is in meteorology for tracing the movements of labelled air masses. The above are but examples of possible applications of the invention. Examples of suitable tracers are sulphur hexafluoride and perfluoro compounds of the elements sulphur, carbon and nitrogen and their combinations. The invention effects the separation of such tracers from other electron absorbers, such as oxygen in the flow to the detector.

We claim:

1. An apparatus for detecting electron absorbing tracer material of interest from a multi-component atmosphere, said apparatus comprising:

an electron capture detector;

conduit means defining a flow path for channeling an atmospheric flow to said electron capture detector, said conduit means including a catalytic reactor, said catalytic reactor having a housing forming a part of said conduit means, said housing being formed from a material selected from the group consisting of palladium and palladium alloys enabling the diffusion of hydrogen therethrough;

means defining a supply of hydrogen;

means for introducing said hydrogen from said supply means directly into said conduit means and thereby into the atmospheric flow upstream of said catalytic reactor, and with said catalytic reactor including a catalyst capable of promoting the combination of hydrogen from said supply means and oxygen from said atmospheric flow to form water vapor in an exothermic reaction;

means downstream from said catalytic reactor for removing water vapor from the atmospheric flow prior to its entry into said electron capture detector;

means operatively associated with said catalytic reactor for retaining at least a portion of the heat released from said exothermic reaction in said catalytic reactor; and means for distributing said retained heat, said means including conducting means disposed centrally within said catalytic reactor, such that the temperature of said atmospheric flow is raised and distributed whereby unwanted electron absorbing components are eliminated from the atmospheric flow thereby permitting the passage of said tracer materials of interest to said electron capture detector.

2. An apparatus as recited in claim 1 wherein said catalyst comprises palladized aesbestos.

* * * * *